United States Patent [19]
Lindqvist et al.

[11] Patent Number: 6,051,747
[45] Date of Patent: Apr. 18, 2000

[54] WOUND DRESSING AND MANUFACTURING METHOD THEREFOR

[75] Inventors: Bengt W. Lindqvist, Lerum; Stefan Areskoug; Thomas Fabo, both of Mölnlycke, all of Sweden

[73] Assignee: Molnlycke Health Care AB, Gothenburg, Sweden

[21] Appl. No.: 08/973,776

[22] PCT Filed: May 2, 1997

[86] PCT No.: PCT/SE97/00738

§ 371 Date: Jan. 6, 1998

§ 102(e) Date: Jan. 6, 1998

[87] PCT Pub. No.: WO97/42985

PCT Pub. Date: Nov. 20, 1997

[30] Foreign Application Priority Data

May 14, 1996 [DE] Germany .................. 9601853

[51] Int. Cl.[7] ........................................... A61F 5/00
[52] U.S. Cl. ........................... 602/46; 602/41; 602/56
[58] Field of Search ............................. 602/41, 46, 55, 602/56

[56] References Cited

U.S. PATENT DOCUMENTS 5,540,922 7/1996 Fabo .
5,635,201 6/1997 Fabo .

*Primary Examiner*—John G. Weiss
*Assistant Examiner*—Kelvin Hart
*Attorney, Agent, or Firm*—Young & Thompson

[57] ABSTRACT

A wound dressing (1) comprising a layer of absorbent foam material (2) which includes a pattern of holes (4). The holes open out on that side of the foam material which lies proximal to the wearer's skin when the dressing (1) is worn, and the layer of foam material is coated with a layer (3) of skin-adhering hydrophobic gel, wherein those end parts of the walls of the holes in the foam material that lie proximal to the wearer's skin when the dressing is worn are gel coated. A method of producing such a dressing is also disclosed.

16 Claims, 2 Drawing Sheets

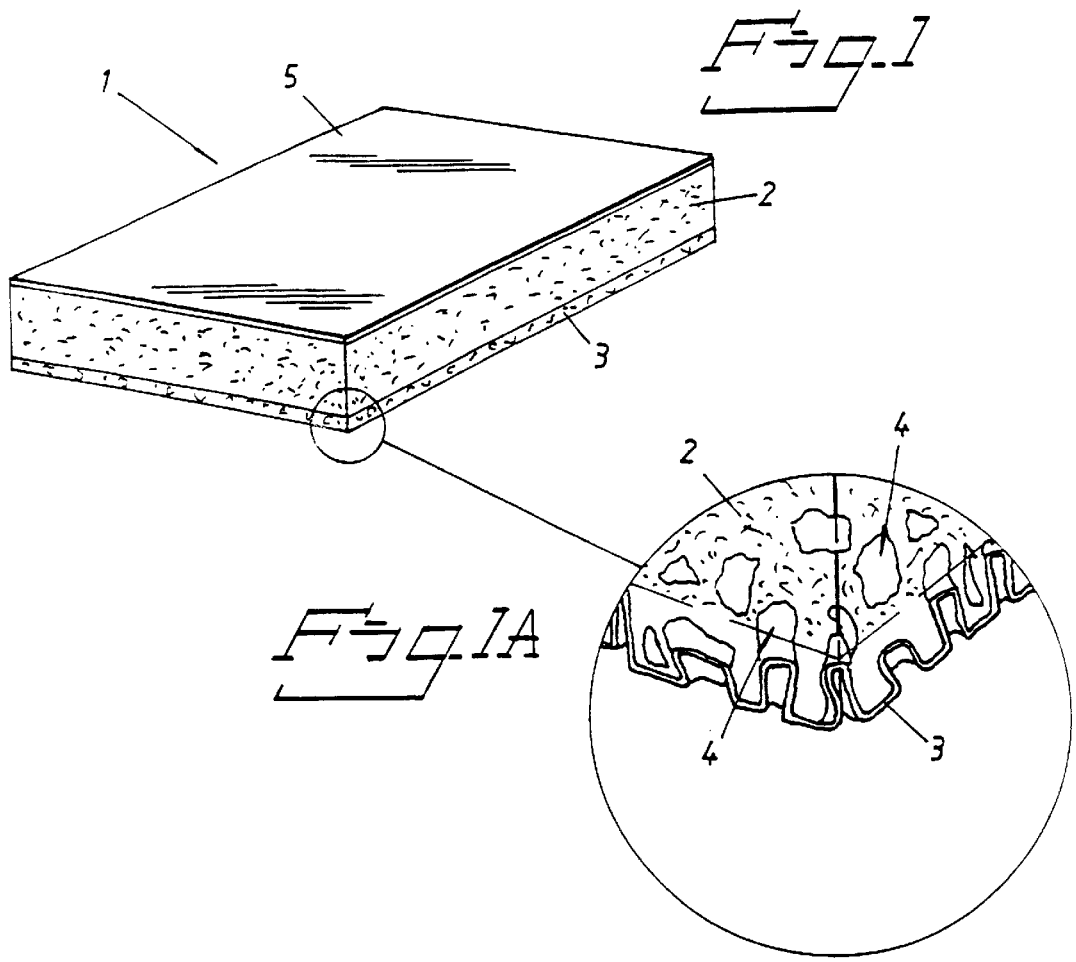
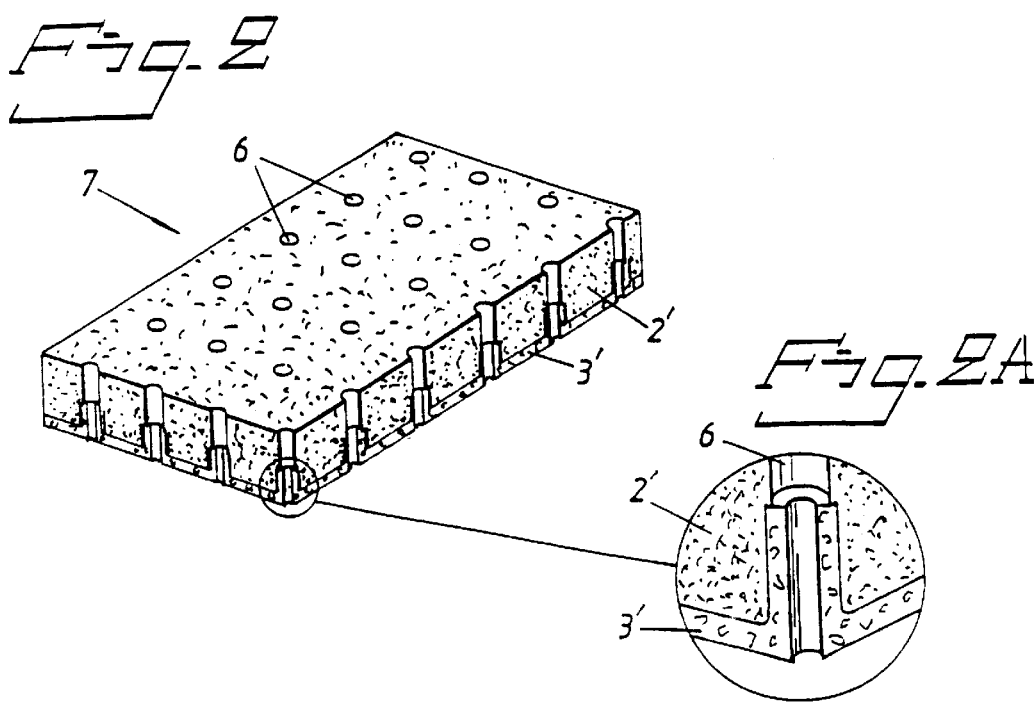

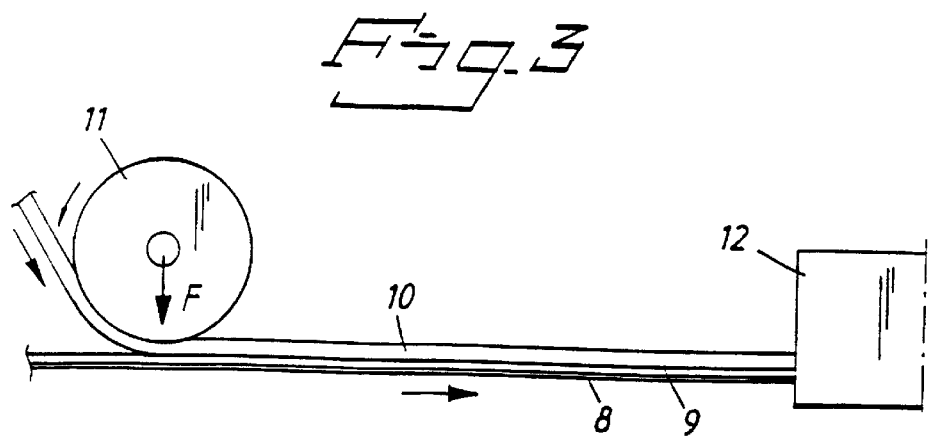
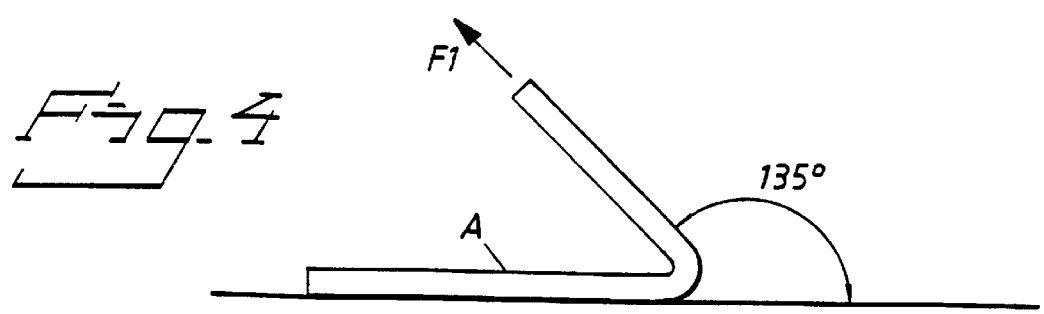
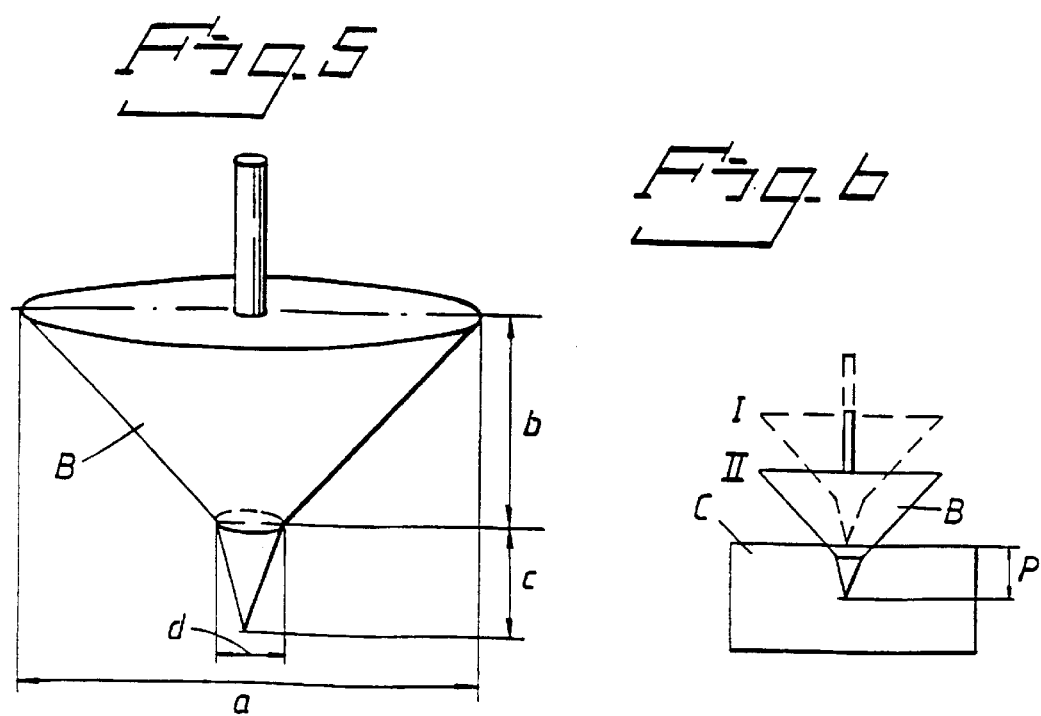

WOUND DRESSING AND MANUFACTURING METHOD THEREFOR

FIELD OF THE INVENTION

The present invention relates to a wound dressing and to a method of its manufacture.

BACKGROUND OF THE INVENTION

European Patent Specification 0 261 167 teaches a wound dressing that has a layer of silicone gel on that side which lies proximal to the wound in use. One of the advantages afforded by such a layer is that it will adhere to dry skin, but not to the surface of a wound. The gel layer is preferably perforated to enable excess fluid exuded by the wound to be absorbed into in an absorbent body placed on top of the gel layer by suction. The perforated pattern in the gel layer is obtained by supporting said layer on a carrier that includes a pattern of holes, such as a knitted textile material or a perforated plastic film.

SUMMARY OF THE INVENTION

The object of the present invention is to provide a wound dressing for weeping sores whose properties are equally as good or better than the properties of the aforedescribed dressing, and which has a simpler construction and which can be produced much more cheaply than the aforesaid dressing.

These objects are achieved in accordance with the invention with a dressing that is characterized by a layer of absorbent foam material that includes a pattern of holes which open into that side of the foam material that lies proximal to the wearer's skin in use, wherein the foam material is coated with a layer of hydrophobic gel which adheres to the skin, and wherein the walls of the holes in the foam material are coated with gel at those end parts of said walls which lie proximal to the wearer's skin when the dressing is used. Because the foam material is used as a gel carrier the dressing has a simpler construction and can be produced more easily than earlier known dressings of this kind. Even a thin gel layer will function as a spacer layer, because it covers an end part of the hole walls and therewith prevents contact between foam material and skin, which reduces material requirements and therewith the cost of the dressing. Because of its hydrophobicity, the spacer layer will prevent spontaneous reflux of absorbed fluid to the skin or the wound.

In a first preferred embodiment intended for wounds from which fluid is exuded only slightly or in normal quantities, the holes of the hole pattern are comprised of the pores in the foam material, wherein the gel also extends slightly into the open pores of the foam material that border on the gel layer, without closing all pores.

In a second preferred embodiment intended for wounds that exude fluid in normal to copious quantities, the holes in the hole pattern are created in the foam material and are through-penetrating.

The foam material is coated with a layer of liquid-impervious material on that side of the foam material that lies distal from the wearer's skin in use.

The dressing has a skin adhesion force F1 of 0.1–2.0 N, suitably 0.3–1.3 N and preferably 0.4–1.0 N. The foam material is a soft, open-cell foam and the gel layer consists of chemically cross-linked hydrophobic silicone gel.

The invention also relates to a method of manufacturing a wound dressing that comprises a layer of absorbent foam material that includes a pattern of holes, wherein the holes open out in that side of the foam material that lies proximal to the wearer's skin when the dressing is used, and wherein the foam material is coated with a layer of skin-adhering gel, and wherein those end portions of the walls of the holes in the foam material that lie proximal to the wearer's skin when the dressing is worn are coated with gel, characterized by placing a sheet of foam material on top of a layer of curable gel mixture, and thereafter heating the gel mixture after a given period of time until the mixture sets.

In a first embodiment the layer of gel mixture has a thickness of 0.1–1.0 mm.

In a second embodiment a pattern of holes is created in the foam material before placing said material on the gel mixture layer.

BRIEF DESCRIPTION OF THE DRAWINGS

The invention will now be described in more detail with reference to the accompanying drawings, in which FIG. 1 is a schematic perspective view of a piece of an inventive dressing according to a first embodiment;

FIG. 1A is an enlarged view of one feature of the FIG. 1 illustration;

FIG. 2 is a view similar to FIG. 1 illustrating a second embodiment of an inventive dressing;

FIG. 2A is an enlarged view of one feature of the FIG. 2 illustration;

FIG. 3 illustrated schematically apparatus for producing a dressing according to FIG. 1 or FIG. 2;

FIG. 4 illustrates schematically a method of determining the adhesiveness of the dressing to the skin;

FIG. 5 illustrates a measuring cone for use in a penetration test; and

FIG. 6 is a schematic illustration of a softness measuring penetration test.

DETAILED DESCRIPTION OF THE INVENTION

FIG. 1 illustrates a piece of a dressing according to a first embodiment of the invention. The dressing is comprised of an absorbent foam material 2 which has been coated with a gel layer 3 on that side which lies proximal to the wound or skin of the wearer when the dressing is used. As illustrated schematically in FIG. 1A, the gel layer 3 is disposed so that even a part of the walls of the open cells or pores 4 in the foam material that open into the gel-coated side thereof are gel coated. Because the gel layer 3 does not close, but only covers, a part of the walls in an end portion of the pores of the foam material that face the wound, excess wound fluid can be drawn into the foam material 2 and absorbed thereby. The gel layer also forms a spacing layer which prevents the foam material from coming into direct contact with the wound or skin of the wearer. The thickness of the total gel layer, i.e. including the depth of penetration into the pores of the foam material, is 0.2–2.0 mm. Some of the pores in the foam material that face towards the wound are closed by the gel layer. The percentage number of pores that are not blocked by the gel layer may vary between 5–100%, depending on the type of wound for which the dressing is intended.

With the intention of providing a dressing that has a dry outer surface, the dressing is given a liquid-impervious layer 5 on the side opposite to the gel layer 3. This liquid-impervious layer 5 may conveniently comprise a thin liquid-impervious, but vador-permeable, plastic film, for instance a polyurethane film.

The foam material 2 is an absorbent foam that has open pores or cells, for instance a polyurethane foam of the type Hypol® from Hampshire Chemical Corporation, Lexington, Mass., USA.

Examples of starting materials and methods suitable for the preparation of appropriate hydrophilic foam are given in U.S. Pat. No. 5,409,472 and in the references cited in this publication. Suitable foam pore sizes may vary between 30 and 1000 $\mu$. Naturally, other types of absorbent foam materials may be used, such as viscose-foam, EVA-foam, hydrophilised silicone foam, etc.

The gel layer 3 is comprised of a chemically cross-linked silicone gel (polydimethyl siloxane gel), for instance a platinum catalyzed 2-component addition hardening RTV-silicone. Examples of gels that can be used are SilGel 612 from Wacker-Chemie GmbH, Burghausen, Germany, and MED-6340 from NuSil Technology, Carpinteria, USA. Examples of adhesive gels useful in this context are also described in GB-A-2 192 142, GB-A-2 226 780 and EP-A1-0 300 620. Other hydrophobic gels are also conceivable, such as hydrophobic polyurethane gels for instance.

The dressing illustrated in FIG. 1 is intended to be used with wounds that exude fluid in quantities ranging from slight to normal. The foam layer has a thickness of 1–10 mm, preferably 2–5 mm. As beforementioned, the foam material functions both as an absorbent and as a gel carrier, and the dressing as a whole will therefore be very soft and pliant. Because the gel adheres to the skin surrounding the wound, the dressing will be held firmly in place while the gel affords a sealing function and prevents maceration, i.e. prevents wound fluid from running over healthy skin and softening the horny layer thereof. The open structure of the gel layer and the foam material also enables the skin to breathe.

The nature of the adhesive gel used in this invention differs totally from the nature of glues that are typically used to secure dressings, for instance the acrylate glues or the hot melt glues that are used today to this end. The significant difference between these glues and the gel used in accordance with the invention is that the gel is much softer and has a better "wetting ability" than said glues. This enables the gels to be given a much lower specific adhesiveness, i.e. lower adhesion per unit of contact surface area, than the specific adhesiveness that must be given to harder glues in order to achieve an equally effective total adhesion as that afforded by the gel. This is associated with the fact that a large surface area is placed under load when peeling soft gel-coated dressings from skin, wherewith the specific adhesion can be maintained at a low level while nevertheless obtaining good total adhesion that will ensure reliable affixation of the dressing. The gels provide a larger load surface partly because they flow down into microscopic cavities and cracks in the skin more effectively than the aforementioned glues, which often cover only a part of the horny layer of the skin, seen in a microscopic perspective. Gels are also able to stretch more and thereby distribute the load over a wider surface area. The stretchability of the soft, flexible gel-carrying foam material also contributes in distributing the load over a wider surface area. The adhesive tapes and dressings normally used in the treatment of wounds, for instance Micropore® (3M), Leukopor® (Beiersdorf), Duo-Derm® (Convatec) or Primapore® (Smithy&Nephiew), require a very high specific adhesiveness in order to provide corresponding total adhesion. High specific adhesion results in a large force at the point where the dressing is pulled from the skin. This is the reason why gel dressings can be formed so that the patient will feel very little pain when the dressing is removed and removal of the dressing can be achieved without stripping cells from the horny layer of the skin, in contradistinction to the effect of glues and adhesive dressings that are typically used. The fact that the gel can be given a lower specific adhesiveness than normal adhesive plasters enables the inventive dressing to be removed from and re-fastened to the skin a number of times without losing the adhesiveness of the dressing to any great extent. Conventional adhesive dressings always lose a greater part of their adhesiveness after being removed only once from the skin, since a large part of the adhesive surface becomes covered with skin residues in the process. The ability to lift-up a dressing for inspection of the wound and to then replace the dressing with retained adhesiveness is both novel and highly advantageous from the aspect of wound treatment. This ability simplifies handling of the dressing and also has a saving effect. The adhesive force between gel and skin is optimized in accordance with the following principle: adhesion shall be as strong as possible without risk of the horny layer of the epidermis being entrained by the gel layer when the dressing is removed. This enables the dressing to be replaced, i.e. the dressing can be removed and replaced several times without deleterious effect to the adhesive properties of the dressing. This is made possible because the softness and flexibility of the gel provides a very wide total contact surface area, which means that the total adhesion of the dressing will be large even when the gel is given a small adhesive force per unit of surface area that will ensure that the horny layers of the epidermis will be left essentially intact when removing the dressing.

In the case of wounds with which the fluid has a high viscosity and is exuded copiously, the open area of the gel layer 3 is insufficient to enable the excess of fluid to be absorbed by the foam material. In this case, the open area is increased by creating in the foam material a pattern of holes that are much larger than the pores or cells of the foam material. FIG. 2 illustrates a dressing intended for wounds that exude fluid in quantities ranging from normal to copious quantities, in which a pattern of holes 6 is created in the foam material 2'. Those components in FIGS. 2 and 2A that find correspondence with the illustration of FIG. 1 have been identified with the same reference signs to which a prime has been added. The dressing 7 thus includes foam material 2' which is coated with a gel layer 3'. As will be evident from FIG. 2, the gel layer 3' extends slightly into the openings 6 and, of course, also into the pores of the foam material 2'. In the case of wounds that exude large quantities of fluid, the dressing 7 may be used together with a further absorbent body (not shown) loosely applied on top of the foam material 2'. This additional absorbent body can then be easily removed, without needing to remove the dressing.

Similar to the dressing 1, the dressing 7 may be provided with a liquid-impervious layer corresponding to the layer 5 of the FIG. 1 embodiment. The holes 6 need not be fully penetrating holes, since it suffices in many cases for the holes to extend partially through the foam material. However, it is necessary that the holes extend to a depth or distance in the foam material that will ensure that the gel layer 3' will not reach the bottoms of the blind holes. The absorption rate of the dressing can be varied, by varying the density of the hole pattern and the size of the holes. A hole pattern also increases the flexibility of the foam material, and therewith also the flexibility of the dressing, even though the holes are not fully penetrating. In a variant not shown in the drawings, the created holes are not penetrating holes but extend only partially into the foam, although to a deeper extent than the gel penetration depth. The gel coating lies on that side in which the holes have been created, and the hole depth is suitably 20–90%, preferably 40–60% of the thickness of the foam layer.

The foam material 2, 2' need not be homogenous, but may be comprised of several superimposed layers of foam material. For instance, a layer of foam material of smaller pore size may be placed outside a layer of larger pore size, so that the outer layer will be saturated first by virtue of the capillary action thus engendered.

FIG. 3 is a highly schematic illustration of apparatus for use in producing an inventive dressing. The illustrated apparatus includes a conveyer (not shown) on which a thin plastic film 8 is conveyed from left to right in FIG. 3. A layer of uncured gel mixture 9 is placed on the film 8. By gel mixture is meant a mixture of those components which form a gel after curing, including polymers that can react with one another to form a cross-linked structure. A layer 10 of absorbent foam material is applied to the layer 9 of uncured gel mixture with the aid of a roller 11, and the layers 9, 10 are then transported into an oven 12. The gel mixture is cured in its passage through the oven 12 and forms a gel layer on the underside of the foam material.

It has been found that with suitable selection of gel mixture, pressure force F, quantity of gel mixture, time between applying foam material and heating the layers, curing temperature, and so on, there will be formed a discontinuous gel coating on the foam material. This is because the gel mixture is drawn by capillary action into those pores or holes in the foam material that open out in that side of the foam material which lies in abutment with the gel mixture. When applying a gel coating to foam material that lacks holes other than pores, the gel mixture must be applied in a layer of such thinness as to ensure that an excessively large number of the pores opening into the underside of the foam material will not be clogged or blocked by the gel coating. The viscosity of the gel mixture and the size of the pores in the foam material also influence the tendency of the mixture to penetrate into the pores. It has been found that the gel mixture layer should preferably be applied to a thickness of 0.1–1,0 mm. A larger part of the gel mixture layer is sucked into the foam, wherewith the total gel layer, including air and foam, will have a thickness of 0.2–2.0 mm.

In a first application of the above method for coating the underside of a polyurethane foam sheet with silicone gel, there was used an open cell, soft hydrophilic polyurethane foam sheet of the type Hydrasorb™ ER from Avitar Inc., Canton, Mass., USA, having a density of 130 kg/m$^3$ and a thickness of 5 mm. The silicone mixture was prepared from SilGel 612 obtained from Wacker, in an A-component and B-component mixing ratio of 1.0:0.9. The uncured mixture had a viscosity of about 1000 mPa. The polyurethane sheet was placed on a silicone mixture having a thickness of 0.2 mm, without applying pressure F from the roller 11, in other words the silicone mixture was subjected solely to the weight of the foam sheet. The time taken to transport the foam material 10 and the underlying silicone mixture 9 from the roller 11 to the oven 12 was one minute and the curing temperature was 130° C. The silicone cured in an oven residence time of 5 minutes. A polyurethane film of high vapor permeability and a thickness of 0.025 mm was then firmly glued to the foam on the side thereof opposite to the gel coating. At this mixture ratio, the silicone gel had a penetration number of 16 mm and the skin adhesion force of the dressing was measured as 0.42 N. Under these conditions, it has been found that the gel mixture layer will preferably have a thickness of at least 0.1 mm, so as to obtain a suitable discontinuous gel coating on the foam material. When the thickness of the gel mixture layer was greater than 0.4 mm, an excessively large percentage of the pores in the foam material became blocked, resulting in insufficient permeability of the gel coating.

It will be evident from the aforegoing that when carrying out the method described with reference to FIG. 3, the quality of the end product will depend on many factors. It is therefore not possible to provide these factors with general limit values, and such limit values must be established empirically with respect to the gel mixture and the foam material used.

A thicker layer of gel mixture can be used with a foam material in which a hole pattern has been created, since the fluid permeability of the gel coating, which constitutes the decisive factor for fluid transportation from a wound to the absorbent foam material, is then determined essentially by the open area of the hole pattern. Closure of the pores on the underside of the foam material will then have only a marginal influence on the course of fluid absorption. In a second application of the aforedescribed method, there is used a polyurethane foam and a silicone gel of the same quality as that described earlier with reference to the first application. However, in this second application through-penetrating cylindrical holes having a diameter of 2 mm and a hole density of 9 holes/cm$^2$ have been formed uniformly in the polyurethane sheet. The process of manufacture was similar to that of the earlier example in other respects, apart from the fact that the thickness of the silicone mixture was increased to 0.4 mm. A polyurethane film of high vapor permeability and a thickness of 0.025 mm was glued finally to the side of the foam that was not coated with silicone.

In the case of copiously weeping open wounds, it has been found that the created holes will suitably have a diameter of 1–3 mm and a hole density of 5–20 holes/cm$^2$, preferably a diameter of about 2 mm and a hole density of 7–12 holes/cm$^2$.

The liquid permeability of the gel coating is suitably varied by adaptation of the density of the hole pattern rather than adaptation of the hole diameter, since the hole diameter influences the course of penetration of the gel mixture into the holes, which the density of the hole pattern does not.

The described method thus enables a dressing of the kind described with reference to FIGS. 1 and 2 to be produced very easily. The method is also very flexible and enables dressings of mutually different absorbencies to be produced in principly the same way and with the aid of the same apparatus.

The force at which a dressing adheres to skin is measured in accordance with the method described below with reference to FIG. 4. At least four strips of dressing A having a width of 25 mm were applied to the backs of at least six persons lying in a horizontal position with their backs uppermost. The dressings were affixed by rolling a cylindrical roller two times over the dressings at a speed of 25 mm/s. The roller had a length of 30 mm and a diameter of 30 mm, and was loaded with a force of 1 N. The strips were left in place for 10 minutes and then peeled-off at a speed of 25 mm/s and with a peeling force F1. The peeling angle, i.e. the obtuse angle defined between skin surface and the removed part of the strip A, shall be 135°, as shown in FIG. 4. In order to obtain a functioning inventive dressing, the peeling force F1 shall be at least 0.1 N. It has also been found that very good functioning of the dressing is obtained when the peeling force F1 is between 0.2 and 1.5 N, preferably 0.4–1.2 N. Corresponding measurements on the shin-adhesion of a conventionally used plaster (Leukopor® from Beiersdorf) gave an adhesion value of 0.29 N.

The ability of the dressing to refasten to the skin after having been removed once was measured by re-fastening the test strips to the same place on the skin after having peeled-off the strips and, after a waiting time of 10 minutes, again peeling-off the strips and measuring the adhesion force. When evaluating the re-fastening ability of samples manufactured in accordance with the first described method, the adhesion force was measured as 0.42 N on the first peeling occasion, and as 0.45 N on the second peeling occasion, indicating that the adhesion force was fully maintained (the difference lies within the statistical error margin). Repeated applications and removals of the same sample piece to/from the same place on the skin showed that the adhesion force remains essentially unchanged over at least five such cycles. Corresponding measurements on the re-fastenability of Leukopor® gave the result 0.29 N after the first peeling occasion and 0.10 N after the second peeling occasion, indicating that adhesion had deteriorated to 35% of the original adhesion. A repeat of the test showed that the adhesive force had fallen almost to zero. This extraordinarily low re-fastenability characterizes all of the conventional adhesive tapes and dressing that were tested, such tapes and dressing often being based on acrylate glue or hot melt glue. In this regard, the adhesion values in respect of the second peeling occasion normally fall to 10–50% of the original value. In order for a dressing in clinical use to function well as a re-fastenable dressing, its adhesion should be at least 80%, suitably at least 90% and preferably at least 95% of the original adhesiveness.

The adhesive force between a dressing produced in accordance with the first described embodiment and polished steel plates measuring 50×125 mm and designed in accordance with the recommendation of ASTM D 3330 M was also measured with a 90° peel adhesion test. This test was carried out as follows: a test strip measuring 25×100 mm was fastened to the steel plate and a pressure roller of rubber A 80 shore with an axial length of 50 mm and weighing 100 g was rolled to and fro over the test strip at a speed of 300 mm/min. The steel plate was placed in a tensile testing machine, e.g. an Instron 4301, so as to lie in a plane that defined an angle of 90° with the direction of pull; i.e. when the pulling direction is vertical, the steel plate is placed horizontally. One end of a paper strip was then fastened to the test strip and the other end of the paper strip was clamped firmly in the upper jaw of the tensile testing machine. After 60 seconds, the test strip was drawn from the steel plate at a speed of 300 mm/min. The position of the steel plate was adjusted during the whole of the peeling process, to ensure that the peeling angle was as close to 90° as possible. The mean force during the tensile test was calculated. At least five test strips were tested. Testing was effected at 23±2° C. and 50±5% RH and the test strips were conditioned under these circumstances for at least 24 hours. In this test, the adhesive force F1 against steel in respect of test strips manufactured in accordance with the first described embodiment was measured to be 0.56 N/25 mm. The adhesive force F1 against steel measured in this way shall be at least 0.15 N/25 mm, suitably in the range of 0.3–2.0 N/25 mm, and preferably 0.6–1.6 N/25 mm for a dressing of this kind.

FIGS. 5 and 6 illustrate a method of measuring the softness of a gel, by allowing a cone B weighing 62.5 g to penetrate a gel sample C of thickness 30 mm gravitationally. The cone B used is shown in FIG. 3 and had the following measurements: a=65 mm, b=30 mm, C=15 mm and d=8.5 mm. The softness of the gel sample was measured by first lowering the cone B to a position I, shown in broken lines in FIG. 6, in which the apex of the cone just touches the surface of the gel sample C. The cone B was then released, so as to be able to penetrate down into the sample C. The distance penetrated by the apex of the cone B after 5 seconds was measured and constitutes the so-called penetration number P, which becomes larger the softer the sample body. Gels having penetration numbers of 5–20 mm, preferably 10–16 mm, have been found suitable for dressing in accordance with the invention.

Foam material that can be considered for use in conjunction with the present invention shall fulfil the flexibility requirement according to ASTM D 3574-86, 3.3.

The described dressing can, of course, be sterilized, e.g. by ethylene oxide sterilization or steam sterilization, and is intended for delivery in different sizes and for different types of wounds, both sterile packed and non-sterile packed. Because of their softness, they are suitable for use in combination with compression bandages and can be used beneficially on blisters, leg ulcers and like wounds. Their high degree of flexibility also makes them suitable for use on joint sores, such as knee sores and elbow sores, even in later phases of the sore healing process. The dressings can also be cut to a size suitable for the size of the sore or wound in question.

It will be understood that the aforedescribed exemplifying embodiments can be modified within the scope of the invention, particularly with respect to the illustrated hole patterns and the described materials. Furthermore, different substances may be mixed in the foam material, for instance active carbon, different salts, pharmacologically acceptable substances, bactericides, etc. Other types of gel mixtures than those described may also be used, for instance gel mixtures which result in a hydrophilic gel when cured. The invention is therefore only restricted by the contents of the following claims.

We claim:

1. A wound dressing, comprising a layer of absorbent foam material which includes a pattern of holes, said holes opening out on that side of the foam material that lies proximal to the skin of a wearer when the dressing is worn, and the layer of foam material being coated with a layer of a skin-adhering hydrophobic gel; and wherein the walls of the holes in said foam material are coated with the gel at those end parts of the holes that lie proximal to the wearer's skin when the dressing is worn.

2. The wound dressing according to claim 1, wherein the holes of the pattern are comprised of pores in said foam material, and the gel also extends partially into open pores of the foam material that border on the gel layer without closing all pores.

3. The wound dressing according to claim 1, wherein the holes in the pattern are created in the foam material.

4. The wound dressing according to claim 3, wherein the holes created in the foam material are through-penetrating.

5. The wound dressing according to claim 3, wherein the holes created in the foam material extend only partially into the foam material.

6. The wound dressing according to claim 1, wherein the foam material is coated with a layer of liquid-impervious material on that side which lies distal from the wearer's skin when the dressing is worn.

7. The wound dressing according to claim 1, wherein the dressing has a skin adhesion force F1 which is greater than 0.1 N.

8. The wound dressing according to claim 7, wherein the skin adhesion force ranges between 0.4 and 1.2 N.

9. The wound dressing according to claim 7, wherein after a first application of the dressing to skin and removal of the dressing therefrom, the dressing can be re-fastened to the skin with essentially the same degree of adhesion as in the first application.

10. The wound dressing according to claim 9, wherein the adhesive force F1 measured on a second dressing-peeling occasion is greater than 80% of the adhesive force F1 measured on the first dressing-peeling occasion.

11. The wound dressing according to claim 1, wherein the foam material is a flexible foam having open pores.

12. The wound dressing according to claim 1, wherein the foam material is a flexible hydrophilic polyurethane foam with open pores.

13. The wound dressing according to claim 1, wherein the gel layer is comprised of a skin adhesive, hydrophobic, cross-linked silicone gel having a penetration number of 5–20 mm.

14. A method of producing a wound dressing comprising a layer of absorbent foam material which includes a pattern of holes, wherein the holes open out on that side of the foam material which lies proximal to the skin of a wearer when the dressing is worn, and the layer of foam material is coated with a layer of skin adhesive gel, and wherein end parts of walls of the holes in the foam material that lie proximal to the wearer's skin when the dressing is worn are gel coated, the method comprising placing a sheet of foam material on top of a layer of curable gel mixture, and then, after a given period of time, heating the gel mixture until the gel mixture has cured.

15. The method according to claim 14, wherein the layer of gel mixture has a thickness greater than 0.1 mm.

16. The method according to claim 14, further comprising creating a patten of holes in the sheet of foam material prior to placing said sheet of foam material on the layer of gel mixture.

* * * * *